United States Patent
Casey et al.

(10) Patent No.: US 9,902,915 B2
(45) Date of Patent: Feb. 27, 2018

(54) IMIDAZOLIUM SULFUR-CONTAINING BINUCLEAR MOLYBDATE SALTS AS LUBRICANT ADDITIVES

(71) Applicant: VANDERBILT CHEMICALS, LLC, Norwalk, CT (US)

(72) Inventors: Brian M. Casey, Norwalk, CT (US); Vincent J. Gatto, Milford, CT (US)

(73) Assignee: VANDERBILT CHEMICALS, LLC, Norwalk, CT (US)

( * ) Notice: Subject to any disclaimer, the term of this patent is extended or adjusted under 35 U.S.C. 154(b) by 0 days.

(21) Appl. No.: 15/432,437

(22) Filed: Feb. 14, 2017

(65) Prior Publication Data

US 2017/0240837 A1 Aug. 24, 2017

Related U.S. Application Data

(60) Provisional application No. 62/298,737, filed on Feb. 23, 2016.

(51) Int. Cl.
| | | |
|---|---|---|
| *C10M 133/06* | (2006.01) | |
| *C10M 125/22* | (2006.01) | |
| *C01G 39/06* | (2006.01) | |
| *C10M 105/60* | (2006.01) | |

(52) U.S. Cl.
CPC ............ *C10M 133/06* (2013.01); *C01G 39/06* (2013.01); *C10M 105/60* (2013.01); *C10M 125/22* (2013.01); *C10M 2215/04* (2013.01); *C10M 2215/224* (2013.01); *C10M 2223/045* (2013.01); *C10N 2210/06* (2013.01); *C10N 2230/06* (2013.01); *C10N 2250/10* (2013.01)

(58) Field of Classification Search
CPC .............. C10M 105/60; C10M 125/22; C10M 133/06; C10M 2215/04; C10M 2215/224; C10M 2223/045; C10N 2210/06; C10N 2230/06; C10N 2250/10; C01G 39/06
See application file for complete search history.

(56) References Cited

U.S. PATENT DOCUMENTS

| | | | |
|---|---|---|---|
| 3,356,702 A | 12/1967 | Farmer | |
| 4,370,245 A | 1/1983 | Ryu et al. | |
| 2010/0227783 A1* | 9/2010 | Habeeb | C10M 141/08 508/262 |
| 2014/0171348 A1 | 6/2014 | Patil et al. | |

FOREIGN PATENT DOCUMENTS

CA  2 831 596 A1  10/2012

OTHER PUBLICATIONS

D. Coucouvanis, A. Toupadakis, A. Hadjikyriacou, "Synthesis of thiomolybdenyl complexes with [Mo2(S)2(O)2]2+ cores and substitutionally labile ligands. Crystal and molecular structure of the tris(dimethylformamide)dioxotetrasulfidodimolybdenum complex", Inorg. Chem, 1988, 27, 3272-3273).*

Asadi et al., "Robust Carbon Dioxide Reduction on Molybdenum Disulphide Edges"; Nature Communications, vol. 5, pp. 1-8, Jul. 2014.

Chen et al., "Synthesis, Spectral, and Structural Characterizations of Imidazole Oxalato Molybdenum(IV/V/VI) Complexes"; Dalton Trans., vol. 42, pp. 1627-1636, 2013.

Coucouvanis et al., "Unique Reactivity Characteristics of MoCoordinated S2 2- and S4 2-Ligands"; Polyhedron, vol. 5 No. 1/2, pp. 349-356, 1986.

International Search Report dated corresponds to international application No. PCT/US17/017799 dated Mar. 28, 2017 dated Apr. 20, 2017.

(Continued)

*Primary Examiner* — James Goloboy
(74) *Attorney, Agent, or Firm* — Norris McLaughlin & Marcus P.A.

(57) ABSTRACT

The present invention relates to a compound of the Formula I:

[Formula I]

$Q_1$

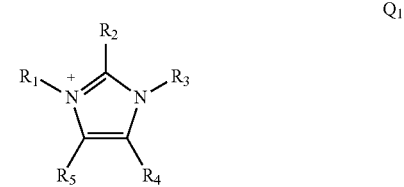

Y
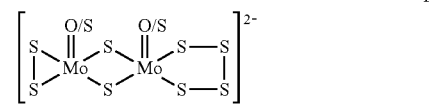

$Q_2$
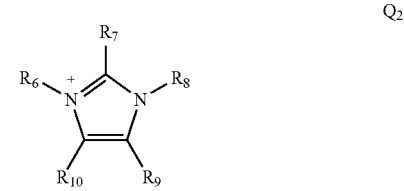

and a lubricating composition containing and a method for preparing the same. In Formula I, $R_1$-$R_5$ and $R_6$-$R_{10}$ are independently selected from the group consisting of hydrogen, hydrocarbyl groups and hydrocarbyl groups containing heteroatoms, such that the total carbon atoms from $Q_1$ and $Q_2$ is from 6 to 166 carbon atoms, and molybdate anion (Y) is a binuclear sulfur-containing dianion selected from the group consisting of $[Mo_2S_8O_2]^{2-}$, $[Mo_2S_9O]^{2-}$, and $[Mo_2S_{10}]^{2-}$.

13 Claims, No Drawings

(56) References Cited

OTHER PUBLICATIONS

Coucouvanis et al., "Synthesis of Thiomolybdenyl Compleses with Mo2(S)2(O)2]2+ Cores and Substitutionally Labile Ligands. Crystal and Molecular Structure of the [Mo2O2S4(DMF)3] Complex", (Inorg. Chem. 1988, vol. 27, pp. 3272-3273).
Coucouvanis et al. and Recatalá et al., "Reaction of MoO42- and WO42- with Aqueous Polysulfides: Synthesis, Structure, and Electrochemistry of η2-Polysulfido Complexes Containing a Bridging S,S {M2O2S2}2+ (M=Mo, W) Core" (Dalton Trans., 2013, 42, 12947-12955).

\* cited by examiner

IMIDAZOLIUM SULFUR-CONTAINING BINUCLEAR MOLYBDATE SALTS AS LUBRICANT ADDITIVES

BACKGROUND

Field of the Invention

This invention concerns compounds useful as an additive in lubricants and greases for friction reduction, wear reduction, and/or extreme pressure performance, among other applications described in detail in this application.

Described herein is the development of highly sulfurized binuclear molybdate salts with application as additives in lubricants. This class of compounds may be represented by the following formula:

[Formula I]

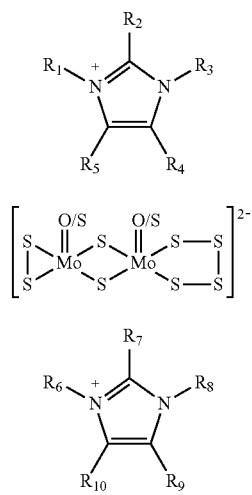

where a molybdenum salt is prepared which comprises two countercations ($Q_1$ and $Q_2$) and a binuclear sulfur-containing molybdate anion (Y).

Discussion of and Comparison with Related Art

This invention involves the preparation and application of imidazolium oxothiomolybdate salts related to a class of compounds described in Coucouvanis et al. (*Inorg. Chem.* 1988, 27, 3272-3273). The compounds described herein are useful as additives in lubricants for friction reduction, wear reduction, and extreme pressure performance. Coucouvanis et al. teach synthesis of thiomolybdenyl complexes with $[Mo_2S_2O_2]^{2+}$ cores and substitutionally labile ligands. Unlike the quaternary ammonium salts prepared in Coucouvanis et al., the compounds described in this application use imidazolium countercations which greatly influence physical properties and performance of the compounds. In all cases reported, the imidazolium oxothiomolybdate salts are room-temperature ionic liquids.

According to U.S. Pat. No. 4,370,245, certain tetrahydrocarbylammonium thiomolybdate containing at least about 15 carbon atoms, such as trioctylmethylammonium thiomolybdate, enhances the extreme pressure properties of substituted-thickened urea greases. The compound used in the invention described herein differs from the compound of the '245 Patent in that the core of the sulfur-containing molybdate structure is distinct from thiomolybdate $(MoS_4)^{2-}$. The molybdenum core of the class of compounds described herein is binuclear with respect to molybdenum and contains oxygen and/or sulfur. Also, the countercations for the described invention are imidazolium-based rather than quaternary ammonium countercations.

U.S. Pat. No. 3,356,702 describes a class of dithiocarbamates having the general formula $MoO_2(SCSNR_2)_2$. The compound used in the invention described herein differs from the compound of the '702 Patent in that the compounds described herein are molybdenum-containing salts rather than neutral organometallic compounds. In addition, the molybdenum-containing salt has higher sulfur to molybdenum ratio than the molybdenum dithiocarbamate technology.

U.S. Patent Application Publication No. 2014/0171348 teaches improving solubility of an ionic liquid in a lubricating oil by using as the lubricating oil a formulated oil including a lubricating oil base stock as a major component and an ionic liquid imidazolium salt base stock as a minor component, which ionic liquid imidazolium salts are represented by the formula:

[Formula II]

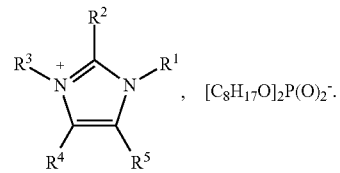

The compound used in the invention described herein differs from the compound of US 2014/0171348 in that the class of compounds described herein involves a molybdenum-containing anion as the counterion for imidazolium-based lubricant additives.

This class of additives improves upon current technology such as molybdenum dithiocarbamates and molybdenum disulfide by increasing the sulfur to molybdenum ratio. These high-sulfur containing additives can exhibit good performance in terms of friction reduction, wear reduction, and/or extreme pressure properties. Furthermore, use of imidazolium as countercations to the oxothiomolybdate dianions results in products that are predominantly room-temperature ionic liquids. Such compounds may have applications beyond lubricants and greases. For example, these compounds can have applications in areas including but not limited to polymer additives, paint additives, specialized solvents and lubricants, refinery chemicals, dissolution and transport of reactive gases (US 2006060818, US 2006060817), metal plating processes (U.S. Pat. No. 4,446,331, U.S. Pat. No. 4,446,350, U.S. Pat. No. 4,446,349), electropolishing of steel surfaces (US 20040097755), antistatic cleaning agents for surfaces, surfactant technologies (WO 2006111712), catalysts and co-catalysts, electrochemical devices, electrolytes for solar cells (U.S. Pat. No. 5,350,644), fuel cells, batteries, high shear mixing technologies (US 20050119423), and extraction (most notably the biphasic acid scavenging using ionic liquids "BASIL™" process developed by BASF, —US 20040073035, US 20050020857, US 20080083606) and separation (US 20040133058) processes. In addition, a variety of ionic liquids have been used industrially as solvents and additives for numerous reactions in organic synthesis that include but are not limited to the nickel-catalyzed dimerization and oligomerization of alkenes (*J. Mol. Catal*, 1994, 92, 155-

164; US 20050113621), hydrosilylation of alkenes, isomerization processes (U.S. Pat. No. 5,238,889), transition metal-catalyzed cross-coupling reactions, olefin metathesis reactions, carbonylation catalysis (U.S. Pat. No. 6,320,083), electrochemical oxidation of sulfur-containing compounds in naphtha (US 20026338788), alkylation reactions (US 20060135839, US 20040133056), and catalytic hydroformylation (US 20070161829). The unique combination of two ionic materials (imidazolium cations and molybdenum-containing anions) to form a liquid product has significant potential in many future industrial applications. Notably, a few examples have been reported in which ionic liquids have been prepared with mononuclear molybdenum-containing anions for use in organic synthesis in the reduction of sulfoxides (*Tetrahedron Lett.*, 2013, 54, 3765-3768; *New J. Chem.*, 2012, 36, 971-976), desulfurization of natural gasoline (*Mol. Divers.*, 2010, 14,777-787), and oxidation of alcohols (*Adv. Synth. Catal.*, 2005, 347, 231-234).

The preparation methods of the molybdenum-containing salts described in Coucouvanis et al. and Recatalá et al. (*Dalton Trans.*, 2013, 42, 12947-12955) were adapted by the inventors of this application for the preparation of imidazolium sulfur-containing molybdate ionic liquids. The reported procedure was further modified to improve removal of unreacted elemental sulfur. The preparation methods described herein remove excess sulfur from the reaction mixture with an appropriate solvent (i.e. acetonitrile) and avoid a recrystallization step. The extraction solvent and unreacted sulfur can be separated by distillation and recycled in the process.

SUMMARY OF THE INVENTION

The present invention relates to a compound of Formula I:

[Formula I]

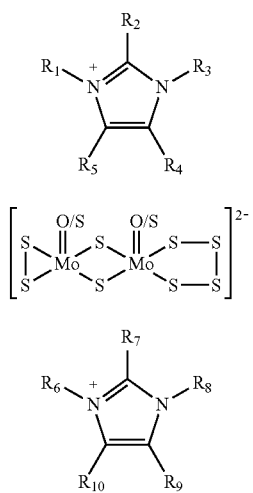

and a lubricating composition containing and a method for preparing the same. In Formula I, $R_1$-$R_5$ and $R_6$-$R_{10}$ are independently selected from the group consisting of hydrogen, hydrocarbyl groups and hydrocarbyl groups containing heteroatoms, such that the total carbon atoms from $Q_1$ and $Q_2$ is from 6 to 166 carbon atoms, and molybdate anion (Y) is a binuclear sulfur-containing dianion selected from the group consisting of $[Mo_2S_8O_2]^{2-}$, $[Mo_2S_9O]^{2-}$, and $[Mo_2S_{10}]^{2-}$. Lubricants containing the novel compound of Formula I as a single component or in combination with other additives have demonstrated improved performance with respect to friction reduction, wear reduction, and/or extreme pressure properties.

DETAILED DESCRIPTION OF THE INVENTION

Lubricants typically require multiple additives in order to improve the overall performance. The class of compounds described in this application when used as a single component additive or in combination with other lubricant additives imparts improved friction reduction, wear reduction, and/or extreme pressure performance over the base lubricant. One advantage of this new imidazolium sulfur-containing molybdate technology is that it allows use of fewer total additives for imparting extreme pressure and antiwear improvements. Another benefit is that it can deliver high levels of both molybdenum and sulfur for boosting extreme pressure and antiwear performance. Another benefit is that the compounds are ionic liquids.

Highly Sulfurized Binuclear Molybdate Salts

Described herein is the development of highly sulfurized binuclear molybdate salts with applications as additives in lubricants. Lubricants containing these additives as a single component or in combination with other additives have demonstrated improved performance with respect to friction reduction, wear reduction, and/or extreme pressure properties. This class of compounds may be represented by the following formula:

[Formula I]

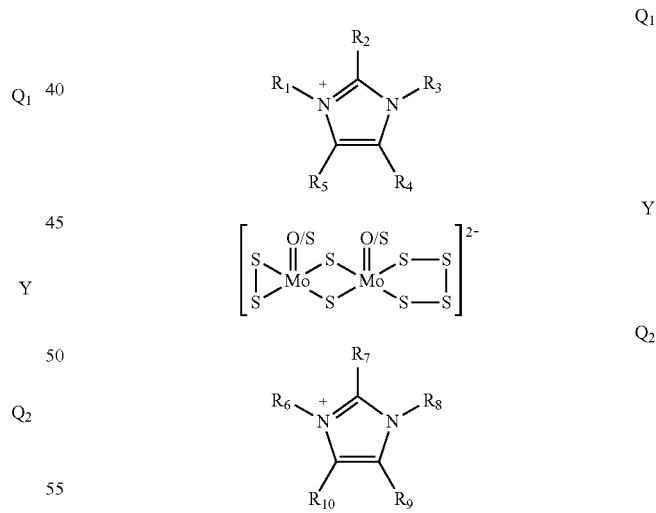

where a molybdenum salt is prepared which comprises two countercations ($Q_1$ and $Q_2$) and a binuclear sulfur-containing molybdate anion (Y). For the countercations, $Q_1$ and $Q_2$ are imidazolium ions comprising groups $R_1$-$R_5$ and $R_6$-$R_{10}$ that are independently selected from hydrogen, hydrocarbyl groups and/or hydrocarbyl groups containing heteroatoms (e.g. oxygen, nitrogen, and sulfur) such that the total carbon atoms from $Q_1$ and $Q_2$ is from 6 to 166, preferably 8-144, 6-64, 6-32, 12-86, or 12-48 carbon atoms. The hydrocarbyl groups can be straight-chain, branched, or cyclic hydrocarbons and saturated or unsaturated hydrocarbons from 0 to 16, preferably 1-16 and more preferably 2-16, 0-10, 0-4 or 1-4 carbon atoms each. The imidazolium countercations can be the same ($Q_1=Q_2$), different ($Q_1 \neq Q_2$), or a mixture of two different countercations of variable ratio (ranging from $Q_1$: $Q_2$=100: 0 to 0 : 100). Molybdate anion (Y) is a binuclear sulfur-containing dianion composed of $[Mo_2S_8O_2]^{2-}$, $[Mo_2S_9O]^{2-}$, $[Mo_2S_{10}]^{2-}$, or mixtures thereof, preferably $[Mo_2S_8O_2]^{2-}$.

In a particular embodiment, the highly sulfurized binuclear molybdate salts include compounds $Q_1=Q_2=$1-ethyl-3-methylimidazolium (emim), 1-n-butyl-3-methylimidazolium (bmim), 1-n-decyl-3-rnethylimidazolium (dmim), or 1,3-di-2-ethylhexylimidazolium (di-2-EHim), and Y=$[Mo_2S_8O_2]^{2-}$, which can be used as lubricant additives at treat rates in the range of 0.1-10.000 wt. %, preferably 0.5-5.00 wt. %, more preferably 1-4.00 wt. %, and yet more preferably 2-4.00 wt.% or 3-4.00 wt.%. In a particularly preferred embodiment, the highly sulfurized binuclear molybdate salt is 1-ethyl-3-methylimidazolium oxothiomolybdate salt, $(emim)_2[Mo_2S_8O_2]$. In an embodiment, molybdenum-containing additives are useful at treat rates sufficient to deliver 100-15,000 ppm, preferably 2800-14,000 ppm, preferably 500-10,000 ppm, more preferably 1,000-10,000 ppm, yet more preferably 5,000-9,000 ppm of molybdenum, and most preferably about 8,400 ppm Mo to the finished lubricant product.

This class of compounds is the product from the reaction of ammonium heptamolybdate tetrahydrate, sulfur, and an imidazolium salt consisting of an imidazolium countercation ($Q_1$ and/or $Q_2$) and an anion. The anion is selected such that the byproduct ammonium salt generated at the end of the reaction is aqueous soluble. Examples of anions include, but are not limited to, halides (fluoride, chloride, bromide, and/or iodide), hydroxide, borates, sulfate, alkylsulfates, bisulfite, sulfite, bicarbonate, carbonates, chlorate, bromate, and/or carboxylates (e.g. acetate). Depending on the identities of $Q_1$ and $Q_2$, the product imidazolium sulfur-containing molybdate salt can be a powder, a low-melting solid (melting point at temperatures 5-50° C.), or a room-temperature ionic liquid. The chemistry of this class of compounds is such that the imidazolium sulfur-containing molybdate salts are predominantly room-temperature ionic liquids. Representative examples for the preparation of the class of compounds of the instant invention are provided in Example 1.

Individual compounds from this class of molecules can be used as additives in lubricants and greases for friction reduction, wear reduction, and/or extreme pressure performance at a treat rate from 0.1-10.000 wt. %, preferably 0.5-5.00 wt. %, more preferably 1-4.00 wt. %, and yet more preferably 2-4.00 wt.% or 3-4.00 wt.%. In an embodiment, molybdenum-containing additives are useful at treat rates sufficient to deliver 100-15,000 ppm, preferably 2,800-14,000 ppm, preferably 500-10,000 ppm, more preferably 1,000-10,000 ppm, yet more preferably 5,000-9,000 ppm, and most preferably about 8,400 ppm of molybdenum to the finished product. Furthermore, these compounds can be used in combination with other additives such as dispersants, detergents, viscosity modifiers, antioxidants, friction modifiers, antiwear agents, corrosion inhibitors, rust inhibitors, salts of fatty acids (soaps), and extreme pressure additives. A preferred application is the use of alkylated-imidazolium binuclear oxothiomolybdates in a lubricant or grease in combination with a zinc-based or phosphorus-based antiwear additive. Examples of zinc-based antiwear additives include zinc dialkyldithiocarbamate (VANLUBE® AZ, VANLUBE® ZDC) and zinc carboxylate (VANLUBE® LVZ). Examples of phosphorus-based antiwear additives include triphenyl phosphate, triphenyl thiophosphate (IRGALUBE® TPPT), trialkylphenyl thiophosphate (IRGALUBE® 211, IRGALUBE® 232), 1,2-dicarbobutoxyethyl-o,o-dialkylphosphorodithioate dialkyl fumarate (VANLUBE® 7611 M, VANLUBE® 727), amine salts of alkyl acid phosphates (VANLUBE® 672, VANLUBE® 672 E, VANLUBE® 692, VANLUBE® 692 E, VANLUBE® 9123, IRGALUBE® 349) alkyl 3-[[bis(1-methylethoxy)phosphinothioyl]thio]propionate (IRGALUBE® 63), antimony 0,0-dialkylphosphorodithioate (VANLUBE® 622), and dialkylphosphite (IRGALUBE® OPH). An example of a zinc- and phosphorus-based anti-wear additive is zinc dialkyldithiophospate (ZDDP or ZDTP). It may be necessary, in certain applications, to use these alkylated-imidazolium binuclear oxothiomolybdates in combination with corrosion or rust inhibitors. Examples of corrosion and rust inhibitors that may be used include liquid imidazoline derivatives (VANLUBE® RI-G, AMINE O), liquid alkenyl succinic acid derivatives (VANLUBE® RI-A, IRGACOR® L 12), N-oleyl sarcosine (SARKOSYL® O), benzotriazole, tolutriazole, liquid tolutriazole derivatives (IRGAMET® 39, CUVAN® 303), liquid triazole derivatives (IRGAMET® 30), alkylated diphenylamine derivatives of tolutriazole (VANLUBE® 887, VANLUBE® 887 E), 2,5-dimercapto-1,3,4-thiadiazole derivatives (CUVAN® 484, CUVAN® 826), 5,5-dithiobis(1,3,4-thiadiazole-2(3H)-thione) (VANLUBE® 829), and salts of dinonylnaphthalene sulfonates (VANLUBE® RI-BSN, VANLUBE® RI-CSN, VANLUBE® RI-ZSN). There may be situations where an improvement in oxidative stability of the grease or lubricant is required. In such a situation, supplemental antioxidants would be used.

Examples of antioxidants include alkylated diphenylamines (VANLUBE® 81, VANLUBE® 961, VANLUBE® SS, VANLUBE® NA, IRGANOX® L 57, IRGANOX® L 67, NAUGALUBE® 438 L, NAUGALUBE® 640), hindered phenolic antioxidants (ETHANOX® 4701, ETHANOX® 4702, ETHANOX® 4703, ETHANOX® 4716, IRGANOX® L 135, IRGANOX® L 101, IRGANOX® L 107, IRGANOX® L 109, IRGANOX® L 115, VANLUBE® BHC), butylated hydroxytoluene (BHT), phenyl-a-naphthylamine (PANA), alkylated phenyl-a-naphthylamine (VANLUBE® 1202, IRGANOX® L 06, NAUGALUBE® APAN), derivatives of alkylated phenyl-a-naphthylamine (VANLUBE® 9317), and polymerized 1,2-dihydro-2,2,4-trimethylquinoline (VANLUBE® RD). Additives containing other elements such as tungsten, boron, copper, titanium, calcium, magnesium, lithium, and barium may also be used. Two very useful additives for reducing friction and wear that may be used are sold commercially as VANLUBE® W-324, an organotungsten-based additive, and VANLUBE® 289, an organoboron-based additive.

Additional sulfur chemistry should not be required when formulating a grease or lubricant with these alkylated-imidazolium binuclear oxothiomolybdates as they inherently have such a high level of sulfur. However, if supplemental sulfur is needed it can be added through the use of sulfurized olefins (VANLUBE® SB), sulfurized fats and oils, ashless dithiocarbamates (VANLUBE® 7723, VANLUBE® 981), or 2,5-dimercapto-1,3,4-thiadiazole derivatives (VANLUBE® 871).

Additional molybdenum chemistry should not be required when formulating a grease or lubricant with these imidazolium binuclear oxothiomolybdates as they inherently have such a high level of molybdenum. However, if supplemental molybdenum is needed it can be added through the use of molybdenum dithiocarbamates (MOLYVAN® A, MOLYVAN® 807, MOLYVAN® 822, MOLYVAN® 3000), molybdenum thiophosphates (MOLYVAN® L), or molybdenum ester/amide complexes (MOLYVAN® 855). The combination of these imidazolium binuclear oxothiomolybdates and molybdenum dithiocarbamates is particularly preferred.

Treat levels for all the above mentioned additives known in the art, which can be used in combination with the highly sulfurized binuclear molybdate salts described herein, can vary significantly depending upon the application, additive solubility, base fluid type, and finished fluid performance requirements. Typical treat levels usually vary from 0.005 wt. % to 10.000 wt. %, preferably 0.01-10.000 wt. %, 0.1-10.000 wt. %, or 1-10.000 wt. %, based on the type of finished lubricant being developed.

In embodiments of the present invention, the treat rates for all additives used in combination with molybdenum do not exceed 1.00 wt. %, preferably the treat rates do not exceed 0.5 wt. %.

Base Oils

The base oils employed as lubricant vehicles are typically oils used in automotive and industrial applications such as, among others, turbine oils, hydraulic oils, gear oils, crankcase oils and diesel oils. The base stock may comprises at least 90%, or at least 95% by weight of the total lubricant composition.

Typical lubricant basestocks that can be used in this invention may include natural base oils, including mineral oils, petroleum oils, paraffinic oils and vegetable oils, as well as oils derived from synthetic sources.

In particular, lubricant basestocks that can be used in this invention may be petroleum-based or synthetic stocks including any fluid that falls into the API basestock classification as Group I, Group II, Group III, Group IV, and Group V. The hydrocarbon base oil may be selected from naphthenic, aromatic, and paraffinic mineral oils.

Suitable synthetic oils may also be selected from, among others, ester-type oils (such as silicate esters, pentaerythritol esters and carboxylic acid esters), esters, diesters, polyol esters, polyalphaolefins (also known as PAOS or poly-α-olefins), hydrogenated mineral oils, silicones, silanes, polysiloxanes, alkylene polymers, polyglycol ethers, polyols, bio-based lubricants and/or mixtures thereof.

Grease

Base grease compositions consist of lubricating oil and a thickener system. Generally, the base oil and thickener system will comprise 65 to 95, and 3 to 10 mass percent of the final grease respectively. The base oils most commonly used are petroleum oils, bio-based oils or synthetic base oils. The most common thickener system known in the art are lithium soaps, and lithium-complex soaps, which are produced by the neutralization of fatty carboxylic acids or the saponification of fatty carboxylic acid esters with lithium hydroxide typically directly in the base fluids. Lithium-complex greases differ from simple lithium greases by incorporation of a complexing agent, which usually consists of di-carboxylic acids. The base grease may comprise at least about 90%, preferably at least 95% by weight of a total lubricating composition.

Other thickener systems that can be used in include aluminum, aluminum complex, sodium, calcium, calcium complex, organo-clay, sulfonate and polyurea, etc.

Other Additives

The compounds of the instant invention can be used in combination with additional additives including but not limited to dispersants, detergents, viscosity modifiers, antioxidants, friction modifiers, antiwear agents, corrosion inhibitors, rust inhibitors, salts of fatty acids (soaps), and extreme pressure additives.

Throughout this application, various publications are referred to. Disclosures of these publications in their entireties are hereby incorporated by reference into this application in order to more fully describe the state of the art as of the date of the invention described herein.

It is understood that where a parameter range is provided, all integers within that range, and tenths thereof, are also provided by the invention.

For the embodiments described in this application, each embodiment disclosed herein is contemplated as being applicable to each of the other disclosed embodiment.

This invention will be better understood by reference to the Experimental Details which follow, but those skilled in the art will readily appreciate that the specific experiments detailed are only illustrative of the invention as described more fully in the claims which follow thereafter.

Experimental Details

EXAMPLE 1

Preparation of Compounds of the Instant Invention

The following procedure is a representative example for the preparation of the class of compounds of the instant invention: 7.42 g of ammonium heptamolybdate tetrahydrate is dissolved in 300 mL of water in a 4-neck flask with a mechanical stirrer. Then, 11.16 g of sulfur is dissolved in 52.81 g of a 20% aqueous solution of ammonium sulfide and slowly added to the reaction. The reaction is stirred for 16 hours. A solution of 8.83 g of 1-ethyl-3-methylimidazolium chloride in 150 mL of water is prepared and added dropwise to the reaction mixture via an addition funnel. The reaction is stirred for an additional 2 hours at room temperature. The upper aqueous layer is decanted from the precipitate. Acetonitrile (300 mL) is added to the flask and the mixture is stirred for an additional 30 minutes. The mixture is filtered and the solids are washed with acetonitrile. The acetonitrile is removed from the filtrate by distillation on a rotary evaporator to yield the product as a deep red-black, viscous liquid that contains 26.1 wt. % Mo and 37.2 wt. % S.

In carrying out the above reaction, a variety of imidazolium salts may be used. For example, when 1-ethyl-3-methylimidazolium is employed, the counteranion may be fluoride, chloride, bromide, iodide, hydroxide, borate, carbonate, bicarbonate, bisulfite, sulfite, bisulfonate, sulfate, alkylsulfates, chlorate, bromate, and carboxylate (e.g. acetate). Additional imidazolium countercations (as depicted in Formula I) that may be used include, but are not limited to, saturated, unsaturated, linear, and/or branched 1-alkyl-3-methyimidazolium (e.g. where alkyl is methyl-, propyl-, butyl-, hexyl-, octyl-, 2-ethylhexyl-, decyl, dodecyl-, tetradecyl-, hexadecyl-, and octadecyl-), symmetric 1,3-dialkylimidazolium (e.g. dimethyl-, diethyl-, dipropyl-, dibutyl-, dihexyl-, dioctyl-, di-2-ethylhexyl-, didecyl-, didodecyl-, ditetradecyl-, dihexadecyl-, and dioctadecyl-), asymmetric 1-alkyl-3-alkylimidazolium (e.g, where two different alkyl groups are selected independently from methyl-, ethyl-, propyl-, butyl-, hexyl-, octyl-, 2-ethylhexyl-, decyl-, dodecyl-, tetradecyl-, hexadecyl-, and octadecyl-), and 1-alkyl-3-benzylimidazolium (e.g. methyl-, ethyl-, propyl-, butyl-, hexyl-, octyl-, 2-ethylhexyl-, decyl-, dodecyl-, tetradecyl-, hexadecyl-, and octadecyl-). The imidazolium countercation may also be similarly symmetrically or asymmetrically substituted at the 2-, 4-, and 5-positions (e.g. groups are independently selected from the following: hydrogen-, methyl-, benzyl-, ethyl-, propyl-, butyl, hexyl-, octyl-, 2-ethylhexyl-, decyl-, dodecyl-, tetradecyl-, hexadecyl-, and octadecyl-). Furthermore, substituents on the imidazolium countercations at ring positions 1-5 may be hydrocarbyl groups containing heteroatoms such as oxygen, nitrogen, and sulfur. Examples of these functional groups include, but are not limited to, alkoxy groups (e.g. ethoxy and propoxy), ethers (e.g. alkyl mono- or polyalkoxy alkylethers where the alkoxy can be ethoxy and/or propoxy and the alkyl group can be methyl-, benzyl-, ethyl-, propyl-, butyl-, hexyl-, octyl-, 2-ethylhexyl-, decyl-, dodecyl-, tetradecyl-, hexadecyl-, and octadecyl-), and/or esters (e.g. 2-(acetyloxy)ethyl, 2-(cocoyloxy)ethyl, and 2-(tallowoyloxy)ethyl).

The following exemplary compounds have been prepared where $Q_1=Q_2$ and $Y=[Mo_2S_8O_2]^{2-}$: 1-ethyl-3-methylimidazolium (emim), 1-n-butyl-3-methylimidazolium (bmim), 1-n-decyl-3-rnethylimidazolium (dmim), and 1,3-di-2-ethylhexylimidazolium (di-2-EHim). Table 1 lists the physical properties of a variety of alkylated-imidazolium binuclear oxothiomolybdate salts that were prepared using the general procedure described above:

TABLE 1

| Imidazolium oxothiomolybdate | Mo (wt. %) | S (wt. %) | N (wt. %) | C (wt. %) | H (wt. %) | Mp (° C.)[1] |
|---|---|---|---|---|---|---|
| $(emim)_2[Mo_2S_8O_2]$ | 26.1 | 37.2 | 8.5 | 21.2 | 3.5 | RTIL |
| $(bmim)_2[Mo_2S_8O_2]$ | 23.9 | 35.8 | 7.6 | 25.7 | 3.9 | RTIL |
| $(dmim)_2[Mo_2S_8O_2]$ | 19.4 | 28.7 | 6.7 | 38.0 | 6.3 | RTIL |
| $(di\text{-}2\text{-}EHim)_2[Mo_2S_8O_2]$ | 14.2 | 23.1 | 6.0 | 46.5 | 7.8 | RTIL |
| Molybdenum Dithiocarbamate | Mo (wt. %) | S (wt. %) | N (wt. %) | C (wt. %) | H (wt. %) | mp (° C.) |
| MOLYVAN ® A | 27.0-29.0 | 23.5-25.5 | — | — | — | 258 |

[1]RTIL—Room-temperature ionic liquid

EXAMPLE 1.1

Preparation of Exemplary Compounds

Preparation of $(emim)_2[Mo_2S_8O_2]$ 7.42 g of ammonium heptamolybdate tetrahydrate is dissolved in 300 mL of water in a 3-neck flask with a mechanical stirrer. Then, 11.16 g of sulfur is dissolved in 52.81 g of a 20% aqueous solution of ammonium sulfide and slowly added to the reaction. The reaction is stirred for 20 hours. A solution of 6.16 g of 1-ethyl-3-methylimidazolium chloride in 150 mL of water is prepared and added slowly to the reaction mixture. The reaction is stirred for an additional 2 hours at room temperature. The upper aqueous layer is decanted from the precipitate. Acetonitrile (300 mL) is added to the flask and the mixture is stirred for an additional 30 minutes. The mixture is filtered and the solids are washed with acetonitrile. The acetonitrile is removed from the filtrate by distillation on a rotary evaporator to yield the product as a deep red-black, viscous liquid that contains 26.1 wt. % Mo and 37.2 wt. % S.

EXAMPLE 1.2

Preparation of Exemplary Compounds

Preparation of $(bmim)_2[Mo_2S_8O_2]$ 2.47 g of ammonium heptamolybdate tetrahydrate is dissolved in 100 mL of water in a 2-neck flask with a mechanical stirrer. Then, 3.72 g of sulfur is dissolved in 17.70 g of a 20% aqueous solution of ammonium sulfide and slowly added to the reaction. The reaction is stirred for 20 hours. A solution of 2.15 g of 1-n-butyl-3-methylimidazolium chloride in 45 mL of water is prepared and added slowly to the reaction mixture. The reaction is stirred for an additional 2 hours at room temperature. The upper aqueous layer is decanted from the precipitate. Acetonitrile (100 mL) is added to the flask and the mixture is stirred for an additional 30 minutes. The mixture is filtered and the solids are washed with acetonitrile. The acetonitrile is removed from the filtrate by distillation on a rotary evaporator to yield the product as a deep red-black, viscous liquid that contains 23.9 wt. % Mo and 35.8 wt. % S.

EXAMPLE 1.3

Preparation of Exemplary Compounds

Preparation of $(dmim)_2[Mo_2S_8O_2]$ 7.42 g of ammonium heptamolybdate tetrahydrate is dissolved in 300 mL of water in a 3-neck flask with a mechanical stirrer. Then, 11.16 g of sulfur is dissolved in 52.81 g of a 20% aqueous solution of ammonium sulfide and slowly added to the reaction. The reaction is stirred for 20 hours. A solution of 10.87 g of 1-n-decyl-3-methylimidazolium chloride in 150 mL of warm water is prepared and added slowly to the reaction mixture. The reaction is stirred for an additional 2 hours at room temperature. The upper aqueous layer is decanted from the precipitate. Acetonitrile (300 mL) is added to the flask and the mixture is stirred for an additional 30 minutes. The mixture is filtered and the solids are washed with acetonitrile. The acetonitrile is removed from the filtrate by distillation on a rotary evaporator to yield the product as a deep red-black, viscous liquid that contains 19.4 wt. % Mo and 28.7 wt. % S.

EXAMPLE 1.4

Preparation of Exemplary Compounds

Preparation of (di-2-EHim)$_2$[Mo$_2$S$_8$O$_2$]

8.12 g of a 37 wt. % aqueous solution of formaldehyde was added to a 3-neck flask with a mechanical stirrer and thermocouple. The reaction is cooled in an ice water bath and 25.85 g of 2-ethylhexylamine is added. Next, 6.00 g of acetic acid is added slowly dropwise while maintaining an internal temperature ≤10° C. After the addition is complete, 14.51 g of a 40 wt. % aqueous solution of glyoxal is added to the reaction. The reaction is heated to 35° C. and stirred for 16 hours. The reaction is heated to 110° C. and water is removed under reduced pressure (2.5 in Hg of vacuum). The material is transferred to a separatory funnel and allowed to stand for 2 hours. The bottom layer is collected to yield 1,3-di-2-ethylhexylimidazolium acetate in 90% purity. This material is used directly without further purification.

7.42 g of ammonium heptamolybdate tetrahydrate is dissolved in 300 mL of water in a 3-neck flask with a mechanical stirrer. Then, 11.16 g of sulfur is dissolved in 52.81 g of a 20% aqueous solution of ammonium sulfide and slowly added to the reaction. The reaction is stirred for 20 hours. A solution of 14.81 g of 1,3-di-2-ethylhexylimidazolium acetate in 50 mL of methanol is prepared and added slowly to the reaction mixture. The reaction is stirred for an additional 2 hours at room temperature. The upper aqueous layer is decanted from the precipitate. Acetonitrile (300 mL) is added to the flask and the mixture is stirred for an additional 30 minutes. The mixture is filtered and the solids are washed with acetonitrile. The acetonitrile is removed from the filtrate by distillation on a rotary evaporator to yield the product as a deep red-orange, viscous liquid that contains 14.2 wt. % Mo and 23.1 wt. % S.

EXAMPLE 2

Performance of Additives

Friction and Extreme Pressure Test Methods in Grease

SRV testing was performed according to the ASTM D5707 method (a ball on disc with a 1.00 mm stroke, 200 N, 50 Hz, at 80° C. for 1 hr). The average coefficient of friction and wear volume were determined for each grease formulation. The base grease used was a lithium complex grease manufactured by Citgo and additives were blended into the grease on a hot plate with magnetic stirring for 30 min at 60° C.

4-Ball wear testing was performed according to the ASTM D2266 method (40 kgf, 1,200 rpm, 75° C., 1 hr). In this test, one steel ball is rotated on three fixed, evenly spaced steel balls covered in a grease formulation. The average wear scar diameter for the three fixed steel balls was determined for each formulation. The base grease used was a lithium complex grease manufactured by Citgo and additives were blended into the grease on a hot plate with magnetic stirring for 30 min at 60° C.

4-Ball weld testing was performed according to the ASTM D2596 method (1,800 rpm, 54° C.). In this test, one steel ball is rotated on three fixed, evenly spaced steel balls covered in a grease formulation at increasing loads for 10 s intervals until welding occurs. The weld point, the load at which the welding occurred, was determined for each grease formulation. The base grease used was a lithium complex grease manufactured by Citgo and additives were blended into the grease on a hot plate with magnetic stirring for 30 min at 60° C.

Frictional and Extreme Pressure Performance of Additives

Data for the performance of the imidazolium oxothiomolybdate additives are provided in Tables 2-5, where a "B" indicates a baseline grease formulation, a "C" indicates a comparison prior art formulation, and an "I" represents the inventive formulations. For these studies, all molybdenum-containing additives were added to lithium complex grease at treat rates sufficient to deliver 8,400 ppm of molybdenum to the finished grease. The treat rates for the other additives used in combination with molybdenum were 0.50 wt. %.

In Table 2, a lithium complex grease was treated with MOLYVAN® A and two different imidazolium oxothiomolybdate salts. The data indicate that both salts provided lower coefficients of friction as well as reduced wear volumes when compared to the base grease containing no additive. In addition, when the imidazolium oxothiomolybdate salts were compared to the molybdenum dithiocarbamate (MOLYVAN® A is a molybdenum dibutyldithiocarbamate commercially available from Vanderbilt Chemicals, LLC), equivalent coefficients of friction were obtained. Furthermore, both greases treated with the imidazolium binuclear oxothiomolybdate salts were superior to MOLYVAN® A in terms of reduction in the wear volume. Both imidazolium oxothiomolybdate salts (Table 2, Samples 3I and 4I) provided comparable coefficients of friction while reducing the wear volume when compared to MOLYVAN® A by more than 50 and 45% respectively. Note that MOLYVAN® A is a well-known antiwear and extreme pressure additive used extensively in grease and lubricant applications (molybdenum content 27.0-29.0%, sulfur content 23.5-25.5%). Use of MOLYVAN® A is described in, e.g., U.S. Pat. Nos. 5,612,298, 5,952,273, 6,432,888, and PCT International Application Publication No. PCT/EP1997/005914.

Tables 3-4 describe performance results from the combination of molybdenum-containing additives with other classes of lubricant additives. The data presented in Table 3 are for the combination of molybdenum additives with VANLUBE® 7611 M, an ashless phosphorodithiolate additive used as an antiwear agent. Combinations of VANLUBE® 7611 M with either imidazolium oxothiomolybdate salt (Table 3, Samples 7I and 8I) resulted in significantly lower coefficients of friction when compared to the base grease containing no additives. Furthermore, both imidazolium oxothiomolybdate combinations had wear volumes lower than that of the combination containing MOLYVAN® A. In particular, the wear volume from the combination of VANLUBE® 7611 M and (emim)$_2$[Mo$_2$S$_8$O$_2$] was improved by a factor of over 28 compared to the combination containing MOLYVAN® A. The data for lithium complex grease treated with the combination of molybdenum-containing additives and OLOA® 262, a zinc dialkyldithiophosphate used as an antiwear agent available from ChevronOronite Company LLC, are included in Table 5. For this series, the imidazolium oxothiomolybdate salts in combination with OLOA® 262 significantly reduced the coefficients of friction and the wear volumes when compared to the base grease containing no additives. In addition, the combination of OLOA® 262 and (emim)$_2$[Mo$_2$S$_8$O$_2$1 ] (Table 4, Sample 11I) resulted in a 43% reduction in the wear volume when compared to the grease containing MOLYVAN® A.

Finally, the performance of both (emim)$_2$[Mo$_2$S$_8$O$_2$] and (dmim)$_2$[Mo$_2$S$_8$O$_2$] as extreme pressure additives were evaluated and compared to that of Vanderbilt Chemicals, LLC products MOLYVAN® A, VANLUBE® 829 (5,5-dithiobis-(1,3,4-thiadiazole-2(3H)-thione, an antiwear agent, antioxidant, and extreme pressure additive), and VANLUBE® 972 M (a thiadiazole derivative in polyalkylene glycol, an ashless extreme pressure additive and corrosion inhibitor) (Table 5). The data indicated that both imidazolium oxothiomolybdate salts showed improved performance when compared to MOLYVAN® A in terms of the 4-ball weld load. While the both VANLUBE® 829 and VANLUBE® 972 M outperformed the molybdenum-containing additives as extreme pressure additives, both imidazolium oxothiomolybdate salts had markedly lower wear volumes. These data indicate that $(emim)_2[Mo_2S_8O_2]$ and $(dmim)_2[Mo_2S_8O_2]$ can provide extreme pressure performance with an additional benefit in terms of wear reduction.

TABLE 2

|  | Sample | | | |
| --- | --- | --- | --- | --- |
|  | 1B | 2C | 3I | 4I |
| MOLYVAN ® A |  | 3.00 |  |  |
| $(emim)_2[Mo_2S_8O_2]$ |  |  | 3.21 |  |
| $(dmim)_2[Mo_2S_8O_2]$ |  |  |  | 4.33 |
| Axel Li-Complex | 100.00 | 97.00 | 96.79 | 95.67 |
| Total Molybdenum (ppm) | 0 | 8400 | 8400 | 8400 |
| ASTM D5707 |  |  |  |  |
| Final Friction μ | 0.176 | 0.124 | 0.129 | 0.128 |
| Average Friction μ | 0.173 | 0.117 | 0.121 | 0.118 |
| Wear Volume, μm³ | 4,500,938 | 296,928 | 141,386 | 162,191 |

TABLE 3

|  | Sample | | | |
| --- | --- | --- | --- | --- |
|  | 5B | 6C | 7I | 8I |
| VANLUBE ® 7611 M |  | 0.50 | 0.50 | 0.50 |
| MOLYVAN ® A |  | 3.00 |  |  |
| $(emim)_2[Mo_2S_8O_2]$ |  |  | 3.21 |  |
| $(dmim)_2[Mo_2S_8O_2]$ |  |  |  | 4.33 |
| Axel Li-Complex | 100.00 | 96.50 | 96.29 | 95.17 |
| Total Molybdenum (ppm) | 0 | 8400 | 8400 | 8400 |
| ASTM D5707 |  |  |  |  |
| Final Friction μ | 0.176 | 0.101 | 0.113 | 0.126 |
| Average Friction μ | 0.173 | 0.93 | 0.114 | 0.124 |
| Wear Volume, μm³ | 4,500,938 | 280,723 | 9,809 | 196,496 |

TABLE 4

|  | Sample | | | |
| --- | --- | --- | --- | --- |
|  | 9B | 10C | 11I | 12I |
| OLOA ® 262 |  | 0.50 | 0.50 | 0.50 |
| MOLYVAN ® A |  | 3.00 |  |  |
| $(emim)_2[Mo_2S_8O_2]$ |  |  | 3.21 |  |
| $(dmim)_2[Mo_2S_8O_2]$ |  |  |  | 4.33 |
| Axel Li-Complex | 100.00 | 96.50 | 96.29 | 95.17 |
| Total Molybdenum (ppm) | 0 | 8400 | 8400 | 8400 |
| ASTM D5707 |  |  |  |  |
| Final Friction, μ | 0.176 | 0.063 | 0.125 | 0.124 |
| Average Friction, μ | 0.173 | 0.071 | 0.110 | 0.123 |
| Wear Volume, μm³ | 4,500,938 | 45,028 | 25,442 | 146,111 |

TABLE 5

|  | Sample | | | | | |
| --- | --- | --- | --- | --- | --- | --- |
|  | 13B | 14C | 15C | 16C | 17I | 18I |
| MOLYVAN ® A |  | 3.01 |  |  |  |  |
| VANLUBE ® 829 |  |  | 3.37 |  |  |  |
| VANLUBE ® 972M |  |  |  | 3.37 |  |  |
| $(emim)_2[Mo_2S_8O_2]$ |  |  |  |  | 3.21 |  |
| $(dmim)_2[Mo_2S_8O_2]$ |  |  |  |  |  | 4.33 |

TABLE 5-continued

| | Sample | | | | | |
|---|---|---|---|---|---|---|
| | 13B | 14C | 15C | 16C | 17I | 18I |
| Axel Li-Complex | 100.00 | 96.99 | 96.63 | 96.63 | 96.29 | 95.17 |
| Total Molybdenum (ppm) ASTM D2596 | 0 | 0 | 0 | 0 | 8400 | 8400 |
| 4-Ball Weld, kgf ASTM D2266 | 200 | 250 | 800+ | 500 | 400 | 315 |
| Wear scar, mm | 0.80 | 0.40 | 0.56 | 0.60 | 0.49 | 0.45 |

What is claimed is:

1. A compound of the Formula I:

[Formula I]

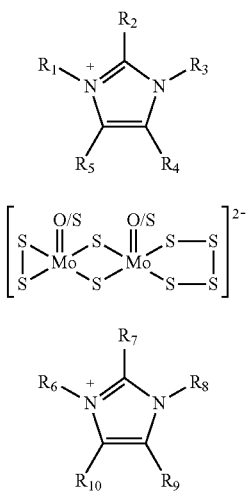

wherein:
$R_1$-$R_5$ and $R_6$-$R_{10}$ are independently selected from the group consisting of hydrogen, hydrocarbyl groups and hydrocarbyl groups containing heteroatoms, such that the total carbon atoms from $Q_1$ and $Q_2$ is from 6 to 166 carbon atoms, and molybdate anion (Y) is a binuclear sulfur-containing dianion selected from the group consisting of $[Mo_2S_8O_2]^{2-}$, $[Mo_2S_9O]^{2-}$, and $[Mo_2S_{10}]^2$.

2. The compound of claim 1, wherein the hydrocarbyl groups are straight-chain, branched, or cyclic hydrocarbons and saturated or unsaturated hydrocarbons from 0 to 16 carbon atoms each.

3. The compound of claim 2, wherein the hydrocarbyl groups have from 1 to 10 carbon atoms each.

4. The compound of claim 1, wherein $Q_1$ and $Q_2$ are the same.

5. The compound of claim 1, wherein $Q_1$ and $Q_2$ are independently selected from the group consisting of 1,3-dimethylimidazolium, 1,3-diethylimidazolium, 1,3-dibutylimidazolium, 1,3-di-2-ethylhexylimidazolium, 1-ethyl-3-methylimidazolium, 1-butyl-3-methylimidazolium and 1-decyl-3-methylimidazolium.

6. The compound of claim 1, selected from the group consisting of (1-ethyl-3-methylimidazolium)$_2$[Mo$_2$S$_8$O$_2$], (1-n-decyl-3-rnethylimidazolium)$_2$[Mo$_2$S$_8$O$_2$], (1-n-butyl-3-methylimidazolium)$_2$[Mo$_2$S$_8$O$_2$], and (1,3-di-2-ethylhexylimidazolium)$_2$[Mo$_2$S$_8$O$_2$].

7. A lubricating composition comprising a lubricant base oil or grease at least 90% by weight of the lubricating composition, and one or more of a compound of claim 1, wherein the compound of Formula I is present in an amount to deliver 100-15,000 ppm of molybdenum to the lubricating composition.

8. The lubricating composition of claim 7, wherein the compound of Formula I is selected from the group consisting of (1-ethyl-3-methylimidazolium)$_2$[Mo$_2$S$_8$O$_2$], (1-n-decyl-3-rnethylimidazolium)$_2$[M$_2$S$_8$O$_2$], (1-n-butyl-3-methylimidazolium)$_2$[Mo$_2$S$_8$O$_2$], and (1,3-di-2-ethylhexylimidazolium)$_2$[Mo$_2$S$_8$O$_2$].

9. The lubricating composition of claim 7, further comprising a phosphorus or nitrogen containing anti-wear compound present at 0.005 wt. % to 10.000 wt. %.

10. The lubricating composition of claim 7, wherein the lubricant base is a grease.

11. The lubricating composition of claim 10, wherein the phosphorus or nitrogen containing anti-wear compound is selected from the group consisting of zinc dialkyldithiocarbamates, zinc dialkyldithiophosphates, dialkyldithiophosphoric acid esters, and amine salts of alkyl acid phosphates.

12. The lubricating composition of claim 10, wherein the grease is lithium complex grease.

13. The lubricating composition of claim 7, wherein the compound of Formula I is selected from the group consisting of (1-ethyl-3-methylimidazolium)$_2$[Mo$_2$S$_8$O$_2$], (1-n-decyl-3-rnethylimidazolium)$_2$[Mo$_2$S$_8$O$_2$], (1-n-butyl-3-methylimidazolium)$_2$[Mo$_2$S$_8$O$_2$], and (1,3-di-2-ethylhexylimidazolium)$_2$[Mo$_2$S$_8$O$_2$] in an amount to deliver 100-15,000 ppm of molybdenum to the lubricating composition, and wherein the grease is a lithium complex grease.

* * * * *

UNITED STATES PATENT AND TRADEMARK OFFICE
CERTIFICATE OF CORRECTION

PATENT NO. : 9,902,915 B2  
APPLICATION NO. : 15/432437  
DATED : February 27, 2018  
INVENTOR(S) : Brian M. Casey et al.

Page 1 of 1

It is certified that error appears in the above-identified patent and that said Letters Patent is hereby corrected as shown below:

On the Title Page

Item [57], "consisting of $[Mo_2S_8O_2]^{2-}$, $[Mo_2S_9O]^{2-}$, and $[Mo_2S_{10}]^{2-}$." should read --consisting of $[Mo_2S_8O_2]^{2-}$, $[Mo_2S_9O]^{2-}$, and $[Mo_2S_{10}]^{2-}$.--

In the Specification

Column 4, Line 1-2, "consisting of $[Mo_2S_8O_2]^{2-}$, $[Mo_2S_9O]^{2-}$, and $[Mo_2S_{10}]^{2-}$." should read --consisting of $[Mo_2S_8O_2]^{2-}$, $[Mo_2S_9O]^{2-}$, and $[Mo_2S_{10}]^{2-}$.--

In the Claims

Claim 1: Column 15, Line 49, "consisting of $[Mo_2S_8O_2]^{2-}$, $[Mo_2S_9O]^{2-}$, and $[Mo_2S_{10}]^{2-}$." should read --consisting of $[Mo_2S_8O_2]^{2-}$, $[Mo_2S_9O]^{2-}$, and $[Mo_2S_{10}]^{2-}$.--

Signed and Sealed this  
Fifth Day of May, 2020

Andrei Iancu  
*Director of the United States Patent and Trademark Office*